US 6,699,462 B2

(12) United States Patent
Seyler et al.

(10) Patent No.: US 6,699,462 B2
(45) Date of Patent: Mar. 2, 2004

(54) ARTIFICIAL TANNING COMPOSITIONS COMPRISING SORGHUM EXTRACTS

(75) Inventors: Nathalie Seyler, Maisons-Alfort (FR); Irène Elguidj, Neuilly (FR); Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 10/338,700

(22) Filed: Jan. 9, 2003

(65) Prior Publication Data

US 2003/0138387 A1 Jul. 24, 2003

(30) Foreign Application Priority Data

Jan. 10, 2002 (FR) .............................. 02 00252
Jan. 10, 2002 (FR) .............................. 02 00253
Jan. 10, 2002 (FR) .............................. 02 00251

(51) Int. Cl.$^7$ ............................. A61K 7/42; A61K 7/44
(52) U.S. Cl. ......................... 424/59; 424/60; 424/400; 424/401
(58) Field of Search ............................. 424/59, 60, 400, 424/401

(56) References Cited

U.S. PATENT DOCUMENTS 6,235,294 B1 * 5/2001 Perrier et al. ............... 424/401
6,471,949 B2 * 10/2002 Candau et al. ................ 424/59
6,558,655 B2 * 5/2003 Candau et al. ................ 424/59

FOREIGN PATENT DOCUMENTS

DE 198 27 976 A1 12/1999
FR 2 757 383 A1 6/1998
FR 2 778 663 A1 11/1999
WO WO 99/25316 A1 5/1999
WO WO 02/41867 A1 5/2002

OTHER PUBLICATIONS

Abstract—XP-002214398 & Cereal Chemistry, vol. 70, No. 6, 1993, pp. 759–760, Database Accession No. PREV199497073236.
Abstract—XP-002214397 & JP 63 135310, AN 1998–195805, Database WPI, Week 199828, Derwent Publications Ltd., London, GB.
Abstract—XP-002214396 & CN 1,209,992, AN 1999–338248, Database WPI, Week 199929, Derwent Publications Ltd., London, GB.
French Search Report Issued on Sep. 24, 2002 Corresponding to FR 02/00251, 3 Pages.
French Search Report Issued on Sep. 24, 2002 Corresponding to FR 02/00252, 3 Pages.
French Search Report Issued on Sep. 24, 2002 Corresponding to FR 02/00253, 2 Pages.

* cited by examiner

Primary Examiner—Shelley A. Dodson
(74) Attorney, Agent, or Firm—Burns, Doane, Swecker & Mathis, L.L.P.

(57) ABSTRACT

Topically applicable, cosmetic/dermatological artificial tanning compositions devoid of certain flavylium salts contain an effective artificial tanning amount of at least one sorghum extract formulated into a topically applicable, cosmetically/dermatologically acceptable vehicle therefor.

23 Claims, No Drawings

ARTIFICIAL TANNING COMPOSITIONS COMPRISING SORGHUM EXTRACTS

CROSS-REFERENCE TO PRIORITY/PROVISIONAL APPLICATIONS

This application claims priority under 35 U.S.C. § 119 of FR-02/00251, FR-02/00252 and FR-02/00253, each filed Jan. 10, 2002, and of provisional applications Serial Nos. 60/350,343, 60/350,356 and 60/350,357, each filed Jan. 24, 2002, each of which is hereby expressly incorporated by reference. This application is also a continuation of said '343, '356 and '357 provisionals.

CROSS-REFERENCE TO COMPANION APPLICATION

Copending application Ser. No. 10/338,713, filed concurrently herewith and assigned to the assignee hereof.

BACKGROUND OF THE INVENTION

1. Technical Field of the Invention

The present invention relates to cosmetic and/or dermatological compositions intended for artificially coloring the skin, characterized in that they comprise, in a cosmetically acceptable vehicle, at least one sorghum extract; the said compositions not containing a flavylium salt which is unsubstituted in position 3 and which is substituted with at least one hydroxyl or alkoxy radical.

The invention also relates to its uses for the manufacture of cosmetic or dermatological compositions for coloring the skin.

2. Description of the Prior Art

Nowadays, it is important to look healthy and a tanned skin is always a sign of good health. However, a natural tan is not always desirable since it requires prolonged exposure to UV radiation, in particular to UV-A radiation which causes the tanning of the skin but, however, is liable to induce an adverse change therein, in particular in the case of sensitive skin or of skin which is continually exposed to solar radiation. It is thus desirable to find an alternative to a natural tan which is compatible with the requirements of such skin types.

Most of the cosmetic products intended for artificially tanning the skin are based on carbonyl derivatives which, by interacting with the amino acids in the skin, allow the formation of colored products.

To this end, it is known that dihydroxy-acetone, or DHA, is a particularly advantageous product which is commonly used in cosmetics as an agent for artificially tanning the skin; when applied to the skin, in particular to the face, it gives a tanning or bronzing effect which is similar in appearance to that which may result from prolonged exposure to sunlight (a natural tan) or under a UV lamp.

A drawback of DHA is the length of time the coloration takes to develop: specifically, several hours (3 to 5 hours in general) are required for the coloration to be revealed. There is thus an increasing demand for fast-acting self-tanning products which give a coloration closer to that of a natural tan.

Thus, efforts are continually being made to find novel compounds and novel compositions which can give the skin an artificial coloration close to that of a natural tan in a simple, effective, fast and risk-free manner.

Sorghum extracts have been known for a long time as food colorants. They give a reddish brown color and have in their composition flavonoids, anthocyanidins and tannins.

SUMMARY OF THE INVENTION

Now, after considerable research conducted in the field of artificial coloring of the skin, the Applicant has discovered that the use as skin-coloring agent of at least one sorghum extract, in the absence of a flavylium salt which is unsubstituted in position 3 and which is substituted with at least one hydroxyl or alkoxy radical, makes it possible to give the skin, immediately after applying the product to it, an artificial coloration close to that of a natural tan.

The subject of the present invention is therefore a novel cosmetic and/or dermatological composition, intended for artificially coloring the skin close to a natural tan, characterized in that it comprises, in a cosmetically acceptable vehicle, at least one sorghum extract; the said composition not containing a flavylium salt which is unsubstituted in position 3 and which is substituted with at least one hydroxyl or alkoxy radical.

A subject of the present invention is also the novel use of at least one sorghum extract in a cosmetic composition not containing a flavylium salt which is unsubstituted in position 3 and which is substituted with at least one hydroxyl or alkoxy radical, with the aim of giving the skin an artificial coloration close to that of a natural tan.

A subject of the present invention is also a process for giving the skin an artificial coloration close to that of a natural tan, characterized in that it consists in applying to the skin an effective amount of a cosmetic composition as defined above.

The compositions and uses in accordance with the invention make it possible to obtain an artificial coloration close to that of a natural tan in a short space of time. Thus, an immediate coloration is obtained, which allows the application to be visualized and consequently allows more uniform spreading of the composition on the skin and thus of the resulting coloration. Moreover, the artificial coloration obtained on the skin according to the invention is extremely close to that of a natural tan.

For the purposes of the present invention, the expression "composition intended for artificially coloring the skin" will be understood to mean a formulation with a particular affinity for the skin which allows it to give the skin a long-lasting coloration, which is non-covering (that is to say which does not have a tendency to opacify the skin) and which is not removed either with water or with a solvent, and which withstands both rubbing and washing with a solution containing surfactants. Such a long-lasting coloration is thus distinguished from the superficial and transient coloration provided, for example, by a make-up product.

Other characteristics, aspects and advantages of the present invention will become apparent on reading the detailed description which follows.

DETAILED DESCRIPTION OF BEST MODE AND SPECIFIC/PREFERRED EMBODIMENTS OF THE INVENTION

The compositions in accordance with the present invention make it possible to obtain, 30 minutes after application to a fair skin at a rate of 2 mg/cm$^2$, a darkening characterized in the (L*, a*, b*) calorimetric measuring system by a ΔL* ranging from −0.5 to −20. Preferably, ΔL* will range from −0.5 to −15.

The compositions in accordance with the present invention give, 30 minutes after application to a fair skin at a rate of 2 mg/cm$^2$, a coloration defined in the (L*, a*, b*) calorimetric measuring system by a ratio Δa*/Δb* ranging from 0.5 to 3 and even more particularly ranging from 0.8 to 2.

According to the present invention, the term "fair skin" means an untanned skin whose calorimetric characteristics may be defined by its ITA angle as defined in the publication by A. Chardon et al., "Skin Color Typology and Suntanning Pathways" presented at the 16th IFSCC congress, Oct. 8–10, 1990, New York, and in *Int. J. Cosm. Sci.* 13 191–208 (1991). The fair skins as defined in this classification have an ITA angle of between 35 and 55.

In the (L*, a*, b*) calorimetric measuring system:

L* represents the luminance or clarity, a* represents the red-green axis (−a*=green, +a*=red) and b* represents the yellow-blue axis (−b*=blue, +b*=yellow). Thus, a* and b* express the shade of the skin.

ΔL* reflects the darkening of the color: the more negative the ΔL*, the darker the color, with:

$$\Delta L^* = L^* \text{ uncolored skin} - L^* \text{ colored skin}.$$

The ratio Δa*/Δb* reflects the red/yellow balance and thus the shade, with:

$$\Delta a^* = a^* \text{ uncolored skin} - a^* \text{ colored skin}$$

$$\Delta b^* = b^* \text{ uncolored skin} - b^* \text{ colored skin}.$$

The sorghum extracts in accordance with the invention are obtained from the whole plant, the stems, the seeds or the leaves of the genus Sorghum. The preferred species of sorghum are chosen from *Sorghum bicolor, Sorghum caudatum, Sorghum nervosum, Sorghum durra, Sorghum vulgare* and the Sorghum species in association with *Colletotrichum graminicola*.

The sorghum extracts in accordance with the invention are more particularly the extracts of *Sorghum vulgare* such as the commercial product Sorghum Extract Absorbance>30 sold by Premier Specialties.

The sorghum extracts in accordance with the invention are obtained from the extraction of the whole plant or of the plant parts cited above which may be in the fresh state or in the dry state.

The sorghum extract in accordance with the invention may be obtained by a process comprising the following steps:

(a) an extraction of the whole plant, the stems, the seeds or the leaves of the genus Sorghum in an aqueous medium which may also contain at least one organic solvent;

(b) a maceration in an alkaline medium having a pH on the order of 11–12;

(c) optionally a precipitation from the maceration medium by addition of an acid so as to reach a pH on the order of 1–2.

The extraction may be carried out in an acidic medium as described in the Chinese patents CN 1035512 C and CN 1064284A and in the publication by M KOUDA-BONAFOS, E CZYZEWSKA, M NACRO and A C OEHLSCHLAGER. "Isolation of apigenin from leaf sheets of *Sorghum caudatum*" Journal of Chemical Ecology, Vol. 20, No. 8, p. 2123–2125 (1995).

It may also be carried out in an alkaline medium followed by precipitation in an acidic medium as described in the Chinese patent CN 1065079A and in the publication by J P REY, J L POUSSET, J LEVESQUE and P WANTY. "Isolation and composition of a natural dye from the stems of *sorghum bicolor* (L.) Moench subsp. *Americanum caudatum*" Cereal Chem. Vol. 70(6), p. 759–760 (1993).

The extraction may also be carried out in an organic medium as described in the publications by J WANG "Studies on extraction of pigment from sorghum husks and its properties" Huaxue Shijie, Vol. 39 (4), p. 211–213 (1998) and by A SEREME, M KOUDA-BONAFOS and M NACRO "Phenolic compounds in *Sorghum caudatum* tissues during plant development" Biomass and Bioenergy Vol. 4(1), p. 69–71 (1993).

The organic solvents used for the extraction may be alcohols such as ethanol, methanol, normal primary propyl alcohol, isopropyl alcohol, normal primary butyl alcohol, propylene glycol and glycerol for example. The organic solvents may also be represented by diethyl ether, acetone, ethyl methyl ketone, ethyl acetate for example. The organic solvents used may also be supercritical fluids or fluorinated solvents such as dodecafluoropentane, tetradecafluorohexane, perfluorinated N-methylmorpholine and methoxynonafluorobutane for example.

Step (b) of maceration in an alkaline medium may be carried out for a period of 15–25 days at a temperature of 60–80° C. in a 0.1N sodium hydroxide solution having a pH on the order of 11–12.

Step (c) of precipitation by addition of acid may be carried out, for example, with 10N hydrochloric acid so as to reach a pH on the order of 1–2. The aqueous suspension thus obtained is then filtered in order to recover the precipitate which is then dried.

Steps (b) and (c) may be repeated several times.

The concentration of sorghum extract in accordance with the invention preferably varies from 0.0001% to 10%, and still more preferably from 0.001% to 5% by weight, relative to the total weight of the composition.

According to a particular form, the compositions according to the invention may additionally contain mono- or polycarbonyl-containing self-tanning agents.

The mono- or polycarbonyl-containing self-tanning agents are chosen, for example, from isatin, alloxan, ninhydrin, glyceraldehyde, mesotartaric aldehyde, glutaraldehyde, erythrulose, pyrazoline-4,5-dione derivatives as described in patent application FR-2,466,492 and WO 97/35842, dihydroxyacetone (DHA), 4,4-dihydroxypyrazoline-5-one derivatives as described in patent application EP-903,342, it being possible for these self-tanning agents to be combined or otherwise with direct dyes or indole derivatives.

In a preferred embodiment of the invention, dihydroxyacetone (DHA) will be more particularly used.

The mono- or polycarbonyl-containing self-tanning agents are generally present in the compositions according to the invention in proportions ranging from 0.1% to 10% by weight relative to the total weight of the composition, and preferably from 0.2% to 8% by weight relative to the total weight of the composition.

According to a particular form, the compositions of the invention may additionally contain one or more ultraviolet radiation screening agents.

The ultraviolet radiation screening agents may be chosen from organic UV screening agents or inorganic UV radiation screening agents.

The organic UV screening agents in accordance with the invention may be water-soluble, fat-soluble or insoluble in the customary cosmetic solvents. They are chosen in particular from anthranilates; cinnamic derivatives; dibenzoylmethane derivatives; salicylic derivatives; camphor derivatives; triazine derivatives such as those disclosed in patent applications U.S. Pat. No. 4,367,390, EP-863,145, EP-517,104, EP-570,838, EP-796,851, EP-775,698, EP-878,469 and EP-933,376; benzophenone derivatives in particular those described in applications EP-A-1,046,391 and DE-10,012,408; benzmalonate derivatives; β,β'-diphenylacrylate derivatives; benzotriazole derivatives; benzimidazole derivatives; imidazolines; bis-benzoazolyl derivatives such as those disclosed in patents EP-669,323 and U.S. Pat. No. 2,463,264; p-aminobenzoic acid (PABA) derivatives; methylenebis(hydroxyphenylbenzotriazole) derivatives as disclosed in patent applications U.S. Pat. Nos. 5,237,071, 5,166,355, GB-2,303,549, DE-19,726,184 and EP-893,119; screening polymers and screening silicones such as those disclosed in particular in patent application WO 93/04665; dimers derived from α-alkylstyrene, such as those disclosed in patent application DE-19,855,649; 4,4-diarylbutadiene derivatives such as those disclosed in patent applications EP-0,967,200, DE-19,755,649, EP-1,333,981 and mixtures thereof.

As examples of organic screening agents, mention may be made of those indicated below under their INCI name:

Para-Aminobenzoic Acid Derivatives:
PABA,
Ethyl PABA,
Ethyl Dihydroxypropyl PABA,
Ethylhexyl Dimethyl PABA sold in particular under the trademark "Escalol 507" by ISP,
Glyceryl PABA,
PEG-25 PABA sold under the trademark "Uvinul P25" by BASF, Salicylic Derivatives:
Homosalate sold under the trademark "Eusolex HMS" by RONA/EM Industries,
Ethylhexyl Salicylate sold under the trademark "Neo Heliopan OS" by Haarmann and Reimer,
Dipropyleneglycol Salicylate sold under the trademark "Dipsal" by Scher,
TEA Salicylate, sold under the name "Neo Heliopan TS" by Haarmann and Reimer, Dibenzoylmethane Derivatives:
Butyl Methoxydibenzoylmethane sold in particular under the trademark "Parsol 1789" by Hoffmann La Roche,
Isopropyl Dibenzoylmethane, Cinnamic Derivatives:
Ethylhexyl Methoxycinnamate sold in particular under the trademark "Parsol MCX" by Hoffmann La Roche,
Isopropyl Methoxycinnamate,
Isoamyl Methoxycinnamate sold under the trademark "Neo Heliopan E 1000" by Haarmann and Reimer,
Cinoxate,
DEA Methoxycinnamate,
Diisopropyl Methylcinnamate,
Glyceryl Ethylhexanoate Dimethoxycinnamate β,β'-Diphenylacrylate Derivatives:
Octocrylene sold in particular under the trademark "Uvinul N539" by BASF,
Etocrylene, sold in particular under the trademark "Uvinul N35" by BASF, Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone, sold under the trademark "Uvinul M40" by BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12

Benzylidenecamphor Derivatives:
3-Benzylidenecamphor manufactured under the trademark "Mexoryl SD" by Chimex,
4-Methylbenzylidenecamphor sold under the trademark "Eusolex 6300" by Merck,
Benzylidenecamphor Sulfonic Acid manufactured under the trademark "Mexoryl SL" by Chimex,
Camphor Benzalkonium Methosulfate manufactured under the trademark "Mexoryl SO" by Chimex,
Terephthalylidene Dicamphor Sulfonic Acid manufactured under the trademark "Mexoryl SX" by Chimex,
Polyacrylamidomethyl Benzylidene Camphor manufactured under the trademark "Mexoryl SW" by Chimex, Phenylbenzimidazole Derivatives:
Phenylbenzimidazole Sulfonic Acid sold in particular under the trademark "Eusolex 232" by Merck,
Benzimidazilate sold under the trademark "Neo Heliopan AP" by Haarmann and Reimer, Triazine Derivatives:
Anisotriazine sold under the trademark "Tinosorb S" by Ciba Geigy,
Ethylhexyl Triazone sold in particular under the trademark "Uvinul T150" by BASF,
Diethylhexyl Butamido Triazone sold under the trademark "Uvasorb HEB" by Sigma 3V,
2,4,6-Tris(diisobutyl 4'-aminobenzalmalonate)-s-triazine, Phenylbenzotriazole Derivatives:
Drometrizole Trisiloxane sold under the name "Silatrizole" by Rhodia Chimie,
Methylene bis-Benzotriazolyl Tetramethylbutylphenol, sold in solid form under the trademark "Mixxim BB/100" by Fairmount Chemical or in micronized form as an aqueous dispersion under the trademark "Tinosorb M" by Ciba Specialty Chemicals, Anthranilic Derivatives:
Menthyl anthranilate sold under the trademark "Neo Heliopan MA" by Haarmann and Reimer, Imidazoline Derivatives:
Ethylhexyl Dimethoxybenzylidene Dioxoimidazoline Propionate, Benzalmalonate Derivatives:
Polyorganosiloxane containing benzalmalonate functional groups sold under the trademark "Parsol SLX" by Hoffmann La Roche 4,4-Diarylbutadiene Derivatives:
1,1-Dicarboxy(2,2'-dimethylpropyl)-4,4-diphenyl-butadiene and mixtures thereof.

The organic UV screening agents most particularly preferred are chosen from the following compounds:
Ethylhexyl Salicylate,
Butyl Methoxydibenzoylmethane,
Ethylhexyl Methoxycinnamate, Octocrylene,
Phenylbenzimidazole Sulfonic Acid,
Terephthalylidene Dicamphor Sulfonic,
Benzophenone-3,
Benzophenone-4,
Benzophenone-5,
4-Methylbenzylidene Camphor,
Benzimidazilate,
Anisotriazine,
Ethylhexyl Triazone,
Diethylhexyl Butamide Triazone,
Methylene bis-Benzotriazolyl Tetramethylbutylphenol,
   1,1-Dicarboxy(2,2'-dimethyl-propyl)-4,4-diphenyl-butadiene
Drometrizole Trisiloxane, and mixtures thereof.

The inorganic screening agents are generally pigments or alternatively nanopigments (average size of the primary particles: generally between 5 nm and 100 nm and preferably between 10 nm and 50 nm) of metal oxides which are coated or uncoated, such as, for example, nanopigments of titanium oxide (amorphous or crystallized in rutile and/or anatase form), of iron oxide, of zinc oxide, of zirconium oxide or of cerium oxide, which are all UV stabilizers that are well known per se. Conventional coating agents are, moreover, alumina and/or aluminum stearate. Such coated or uncoated metal oxide nanopigments are disclosed in particular in patent applications EP-A-0,518,772 and EP-A-0,518,773.

The radiation screening agents in accordance with the invention are generally present in the compositions according to the invention in proportions ranging from 0.1% to 20% by weight relative to the total weight of the composition, and preferably ranging from 0.2% to 15% by weight relative to the total weight of the composition.

The compositions in accordance with the present invention may also comprise conventional cosmetic adjuvants chosen in particular from fatty substances, organic solvents, ionic or nonionic thickeners, softeners, antioxidants, anti-free-radical agents, opacifiers, stabilizers, emollients, silicones, α-hydroxy acids, insect repellents, antifoams, moisturizers, vitamins, fragrances, preserving agents, surfactants, fillers, polymers, propellants, basifying or acidifying agents, coloring agents, or any other ingredient usually used in the cosmetic or dermatological field, in particular for manufacturing antisun compositions in the form of emulsions.

The fatty substances may consist of an oil or a wax or mixtures thereof. The expression wax is understood to mean a compound which is solid or substantially solid at room temperature, and whose melting point is generally greater than 35° C.

As oils, mention may be made of mineral oils (paraffin); vegetable oils (sweet almond, macadamia, blackcurrant seed or jojoba oil); synthetic oils such as perhydrosqualene, alcohols, fatty acids or esters (such as benzoate of $C_{12}$–$C_{15}$ alcohols which is sold under the trademark "Finsolv TN" by Finetex, octyl palmitate, isopropyl lanolate, triglycerides including those of capric/caprylic acids), oxyethylenated or oxypropylenated fatty esters and ethers; silicone oils (cyclomethicone, polydimethylsiloxanes, or PDMS) or fluoro oils, polyalkylenes.

As waxy compounds, mention may be made of paraffin, carnauba wax, beeswax, hydrogenated castor oil.

Among the organic solvents, mention may be made of lower alcohols and polyols.

The latter may be chosen from glycols and glycol ethers such as ethylene glycol, propylene glycol butylene glycol, dipropylene glycol or diethylene glycol.

The thickeners may be chosen in particular from crosslinked polyacrylic acids, modified or unmodified guar gums and celluloses such as hydroxypropylated guar gum, methylhydroxyethylcellulose and hydroxypropylmethylcellulose.

Needless to say, a person skilled in the art will take care to select the abovementioned optional additional compound(s) and/or the amounts thereof such that the advantageous properties intrinsically associated with the use of the compounds of the flavylium salt type in accordance with the invention are not, or are not substantially, adversely affected by the addition(s) envisaged.

The compositions according to the invention may be prepared according to techniques well known to a person skilled in the art, in particular those intended for the preparation of emulsions of the oil-in-water or water-in-oil type.

This composition may be provided in particular in the form of a simple or complex emulsion (O/W, W/O, O/W/O or W/O/W) such as a cream, a milk, or in the form of a gel or a cream-gel, in the form of a lotion, a powder, a solid stick and may be optionally packaged as an aerosol and may be provided in the form of a mousse or a spray.

Preferably, the compositions according to the invention are provided in the form of an oil-in-water or water-in-oil emulsion.

When it is an emulsion, the aqueous phase of this emulsion may comprise a nonionic vesicular dispersion prepared according to known processes (Bangham, Standish and Watkins, J. Mol. Biol. 13, 238 (1965), FR-2,315,991 and FR-2,416,008).

Concrete but in no way limiting examples illustrating the invention will now be given.

EXAMPLE 1

This example is intended to show, firstly, the intensity of the coloration obtained with a sorghum extract in accordance with the present invention and the speed at which this coloration develops compared with a composition containing DHA as skin-coloring agent.

This example is intended to show, secondly, that the coloration obtained with a sorghum extract in accordance with the present invention is close to that of a natural tanning of the skin.

The Applicant prepared the following compositions (the quantities are expressed as a percentage by weight with respect to the total weight of the composition):

Composition $A_1$ (not According to the Invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Propylene glycol | 15 g |
| Preservatives | qs |
| Demineralized water | qs 100 g |

Composition B₁ (Invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Propylene glycol | 15 g |
| Extract of *Sorghum vulgare* (Sorghum Extract Absorbance >30 from Premier Specialties) | 0.7 g |
| Preservatives | qs |
| Demineralized water | qs 100 g |

Protocol for Evaluation:

Composition $A_1$ and $B_1$ were applied at the rate of 2 mg/cm² to an area of 2×2 cm² delimited on the back of the forearm of which the skin color, characterized by the ITA angle, is between 35 and 55.

The following series of colorimetric measurements were taken using a Minolta CM-508d spectrocolorimeter:

1) before applying the composition,
2) 30 minutes after application.

The results are expressed in the (L*, a*, b*) system in which L* represents the luminance, a* represents the red-green axis (−a*=green, +a*=red) and b* represents the yellow-blue axis (−b*=blue, +b*=yellow). Thus, a* and b* express the shade of the skin.

To evaluate the intensity of the coloration, the important value is the ΔL* which reflects the darkening of the color: the more negative the ΔL*, the darker the color, with:

$$\Delta L^* = L^* \text{ uncolored skin} - L^* \text{ colored skin}.$$

For the shade of the coloration obtained, the important value is the ratio Δa*/Δb* which reflects the red/yellow balance and thus the shade, with:

$$\Delta a^* = a^* \text{ uncolored skin} - a^* \text{ colored skin}$$

$$\Delta b^* = b^* \text{ uncolored skin} - b^* \text{ colored skin}$$

TABLE (I)

| | Composition A₁ (comparative) ΔL* | Composition B₁ (invention) ΔL* | Composition B₁ (invention) Δa*/Δb* |
|---|---|---|---|
| T = 30 minutes | −0.4 | −5.6 | 2.7 |

It is thus found that 30 minutes after application, composition $B_1$ containing DHA and the coloring plant extract makes it possible to obtain a darkening which is much more intense than that obtained with composition $A_1$ containing only DHA.

Composition $B_1$ containing DHA and the coloring plant extract also makes it possible to obtain a shade close to a natural tan.

EXAMPLE 2

The procedure is carried out under the same conditions as in Example 1.

Composition A₂ (not According to the Invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Propylene glycol | 15 g |
| Preservatives | qs |
| Demineralized water | qs 100 g |

Composition B₂ (Invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Propylene glycol | 15 g |
| Extract of *Sorghum vulgare* (Sorghum Extract Absorbance >30 from Premier Specialties) | 0.7 g |
| Dihydroxyacetone | 4 g |
| Preservatives | qs |
| Demineralized water | qs 100 g |

The results obtained are collated in table (II) below:

TABLE (II)

| | Composition A₂ (comparative) ΔL* | Composition B₂ (invention) ΔL* | Composition B₂ (invention) Δa*/Δb* |
|---|---|---|---|
| T = 30 minutes | −0.4 | −5 | 1.2 |

It is thus found that 30 minutes after application, composition $A_2$, which contains only DHA as skin-coloring agent, gives the skin only a very faint coloration, since the DHA has not yet had time to act (Δl*=−0.4). On the other hand, composition $B_2$ according to the invention, containing DHA combined with the sorghum extract, has already given the skin a significant coloration (ΔL*=−5).

Composition $A_2$ does not give after 30 minutes a darkening comparable to that of composition $B_2$.

EXAMPLE 3

The procedure is carried out under the same conditions as in Example 1.

Composition A₃ (not According to the Invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Propylene glycol | 15 g |
| Preservatives | qs |
| Demineralized water | qs 100 g |

Composition B₃ (Invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| 1,4-Benzene[di(3-methylidene-10-camphor-sulphonic)] acid | 0.5 g |
| Propylene glycol | 15 g |
| Extract of *Sorghum vulgare* (Sorghum Extract Absorbance >30 from Premier Specialties) | 0.7 g |

-continued

| | |
|---|---|
| Preservatives | qs |
| Demineralized water | qs 100 g |

The results obtained are collated in table (III) below:

TABLE (III)

| | Composition $A_3$ (comparative) $\Delta L^*$ | Composition $B_3$ (invention) $\Delta L^*$ |
|---|---|---|
| T = 30 minutes | −0.4 | −6.1 |

It is thus found that 30 minutes after application, composition $A_3$, which contains DHA as skin-coloring agent, gives the skin only a very faint coloration, since the DHA has not yet had time to act ($\Delta L^*$=−0.4). On the other hand, composition $B_3$ according to the invention, containing the sorghum extract combined with a UV-screening agent, has already given the skin a significant coloration ($\Delta L^*$=−6.1).

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, cosmetic/dermatological artificial tanning composition, comprising an effective artificial tanning amount of at least one sorghum extract formulated into a topically applicable, cosmetically/dermatologically acceptable vehicle therefor, said composition being devoid of any flavylium salt that is unsubstituted at position 3 thereof, but which is otherwise substituted with at least one hydroxyl group or alkoxy radical.

2. The cosmetic/dermatological artificial tanning composition as defined by claim 1, comprising an amount of said at least one sorghum extract which is effective for obtaining, 30 minutes after application to a fair skin at a rate of 2 mg/cm², a darkening defined in the (L*, a*, b*) calorimetric measuring system by a $\Delta L^*$ ranging from −0.5 to −20.

3. The cosmetic/dermatological artificial tanning composition as defined by claim 2, said $\Delta L^*$ ranging from −0.5 to −15.

4. The cosmetic/dermatological artificial tanning composition as defined by claim 1, comprising an amount of said at least one sorghum extract which is effective for obtaining, 30 minutes after application to a fair skin at a rate of 2 mg/cm², a coloration defined in the (L*, a*, b*) calorimetric system by a ratio $\Delta a^*/\Delta b^*$ ranging from 0.5 to 3.

5. The cosmetic/dermatological artificial tanning composition as defined by claim 4, said ratio $\Delta a^*/\Delta b^*$ ranging from 0.8 to 2.

6. The cosmetic/dermatological artificial tanning composition as defined by claim 1, said at least one sorghum extract being obtained from the whole plant, the stems, the seeds or the leaves of the genus Sorghum, in the fresh or dry state.

7. The cosmetic/dermatological artificial tanning composition as defined by claim 6, the species of Sorghum being selected from among *Sorghum bicolor, Sorghum caudatum, Sorghum nervosum, Sorghum durra, Sorghum vulgare* and the Sorghum species in association with *Colletotrichum graminicola*.

8. The cosmetic/dermatological artificial tanning composition as defined by claim 6, said at least one sorghum extract being obtained from the whole plant, the stems, the seeds or the leaves of *Sorghum vulgare*.

9. The cosmetic/dermatological artificial tanning composition as defined by claim 6, said at least one sorghum extract being obtained by a process comprising:

(a) an extraction of the whole plant, the stems, the seeds or the leaves of Sorghum in an aqueous medium which may also contain at least one organic solvent;

(b) a maceration in an alkaline medium having a pH on the order of 11–12; and (c) optionally, a precipitation from the maceration medium by addition of an acid to attain a pH on the order of 1–2.

10. The cosmetic/dermatological artificial tanning composition as defined by claim 1, in which the concentration of sorghum extract ranges from 0.0001% to 10% by weight, relative to the total weight thereof.

11. The cosmetic/dermatological artificial tanning composition as defined by claim 1, further comprising at least one mono- or polycarbonyl-containing artificial/self-tanning agent.

12. The cosmetic/dermatological artificial tanning composition as defined by claim 11, said at least one mono- or polycarbonyl-containing artificial/self-tanning agent comprising isatin, alloxan, ninhydrin, glyceraldehyde, mesotartaric aldehyde, glutaraldehyde, erythrulose, a pyrazoline-4,5-dione derivative, dihydroxyacetone (DHA), and/or a 4,4-dihydroxypyrazoline-5-one derivative, optionally combined with a direct dye or an indole derivative.

13. The cosmetic/dermatological artificial tanning composition as defined by claim 12, said at least one artificial/self-tanning agent comprising dihydroxyacetone (DHA).

14. The cosmetic/dermatological artificial tanning composition as defined by claim 11, in which the at least one artificial/self-tanning agent is present in a proportion ranging from 0.1% to 10% by weight relative to the total weight of the composition.

15. The cosmetic/dermatological artificial tanning composition as defined by claim 1, further comprising at least one UV radiation screening agent.

16. The cosmetic/dermatological artificial tanning composition as defined by claim 15, said at least one UV radiation screening agent comprising an organic UV screening agent or an inorganic UV radiation screening agent.

17. The cosmetic/dermatological artificial tanning composition as defined by claim 16, comprising at least one organic UV screening agent that is water-soluble, fat-soluble or insoluble in a usual cosmetic solvent.

18. The cosmetic/dermatological artificial tanning composition as defined by claim 17, said at least one organic UV screening agent comprising an anthranilate; a cinnamic derivative; a dibenzoylmethane derivative; a salicylic derivative; a camphor derivative; a triazine derivative; a benzophenone derivative; a β,β'-diphenylacrylate derivative; a benzotriazole derivative; a benzimidazole derivative; an imidazoline; a bis-benzoazolyl derivative; a p-aminobenzoic acid (PABA) derivative; a methylenebis (hydroxyphenylbenzotriazole) derivative; a screening polymer and a screening silicone; a dimer derived from α-alkylstyrene; a 4,4-diarylbutadiene derivative, and mixtures thereof.

19. The cosmetic/dermatological artificial tanning composition as defined by claim 17, said at least one organic UV radiation screening agent comprising:

Ethylhexyl Salicylate,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic,
Benzophenone-3,
Benzophenone-4,
Benzophenone-5,
4-Methylbenzylidene Camphor,
Benzimidazilate,
Anisotriazine,
Ethylhexyl Triazone,
Diethylhexyl Butamido Triazone,
2,4,6-Tris(diisobutyl 4'-aminobenzalmalonate)-s-triazine,
Methylenebis-Benzotriazolyl Tetramethylbutylphenol,
Drometrizole Trisiloxane,
1,1-Dicarboxy(2,2'-dimethyl-propyl)-4,4-diphenylbutadiene, and mixtures thereof.

20. The cosmetic/dermatological artificial tanning composition as defined by claim 16, comprising at least one inorganic UV radiation screening agent selected from among pigments or nanopigments of metal oxides which are coated or noncoated.

21. The cosmetic/dermatological artificial tanning composition as defined by claim 20, said at least one inorganic UV radiation screening agent comprising nanopigments of titanium, iron, zinc, zirconium or cerium oxide, which are coated or uncoated.

22. The cosmetic/dermatological artificial tanning composition as defined by claim 15, in which said at least one UV radiation screening agent is present in a proportion ranging from 0.1% to 15% by weight relative to the total weight thereof.

23. A regime or regimen for the artificial tanning of human skin, comprising topically applying thereon a thus effective amount of the cosmetic/dermatological artificial tanning composition as defined by claim 1.

* * * * *